US00PP31420P3

(12) United States Plant Patent
van Langen

(10) Patent No.: US PP31,420 P3
(45) Date of Patent: Jan. 28, 2020

(54) PACHYVERIA PLANT NAMED 'AMIECH1702'

(50) Latin Name: ***Echeveria lilacina* x *Pachyphytum oviferum***
Varietal Denomination: AMIECH1702

(71) Applicant: NovoAmi B.V., Heerhugowaard (NL)

(72) Inventor: Gerard van Langen, Heerhugowaard (NL)

(73) Assignee: NovoAmi B.V., Heerhugowaard (NL)

( * ) Notice: Subject to any disclaimer, the term of this patent is extended or adjusted under 35 U.S.C. 154(b) by 0 days.

(21) Appl. No.: 15/932,613

(22) Filed: Mar. 23, 2018

(65) Prior Publication Data

US 2019/0297766 P1 Sep. 26, 2019

(51) Int. Cl.
*A01H 5/12* (2018.01)
*A01H 6/32* (2018.01)

(52) U.S. Cl.
USPC ..... Plt./373
CPC ..... *A01H 6/32* (2018.05)

(58) Field of Classification Search
USPC ..... Plt./373
See application file for complete search history.

*Primary Examiner* — Anne Marie Grunberg
(74) *Attorney, Agent, or Firm* — Samuel R. McCoy, Jr.

(57) ABSTRACT

A new and distinct *Pachyveria* hybrid plant named 'AMIECH1702' which is characterized by greyed-green succulent foliage with a blue hue, foliage with is arranged in a compact basal rosette with narrower, more rounded foliage at the center of the rosette and broader, flatter foliage towards the outer foliar whorls of the rosette, and the stability of these characteristics from generation to generation.

4 Drawing Sheets

Latin name of the genus and species: The Latin name of the genus and species of the novel variety disclosed herein is *Echeveria lilacina* x *Pachyphytum oviferum.*

Variety denomination: The inventive variety of *Pachyveria* hybrid disclosed herein has been given the variety denomination 'AMIECH1702'.

BACKGROUND OF THE INVENTION

Parentage: 'AMIECH1702' is an intergeneric hybrid seedling selection resulting from the controlled pollination of an unnamed *Echeveria lilacina* plant (not patented), the seed parent, with an unnamed *Pachyphytum oviferum* plant (not patented), the pollen parent. The crossing was made by the inventor in the spring of 2011 at a commercial greenhouse in Heerhugowaard, the Netherlands. In the summer of 2012, one seedling was observed which exhibited unique growth and foliage characteristics. The seedling was isolated for further evaluation in order to confirm the distinctness and stability of the characteristics first observed. Upon confirmation of distinctness and stability, 'AMIECH1702' was selected for commercialization.

Asexual Reproduction: Asexual reproduction of the new cultivar 'AMIECH1702', by way of rooting leaf cuttings, was first initiated in the summer of 2013 at the inventor's commercial greenhouse in Heerhugowaard, the Netherlands. Through five subsequent generations, the unique features of this cultivar have proven to be stable and true to type.

SUMMARY OF THE INVENTION

The cultivar 'AMIECH1702' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'AMIECH1702'. These characteristics in combination distinguish 'AMIECH1702' as a new and distinct *Pachyveria* hybrid cultivar:

1. 'AMIECH1702' exhibits succulent foliage arranged in a compact basal rosette with narrower, more rounded foliage at the center of the rosette and broader, flatter foliage towards the outer foliar whorls of the rosette; and
2. 'AMIECH1702' exhibits moderately glaucous, greyed-green foliage with a blue hue; and
3. 'AMIECH1702' foliage with an acute to acuminate apex with margins towards the apex are very slightly crenate to sinuate.

BOTANICAL DESCRIPTION OF THE PLANT

Figure 1:
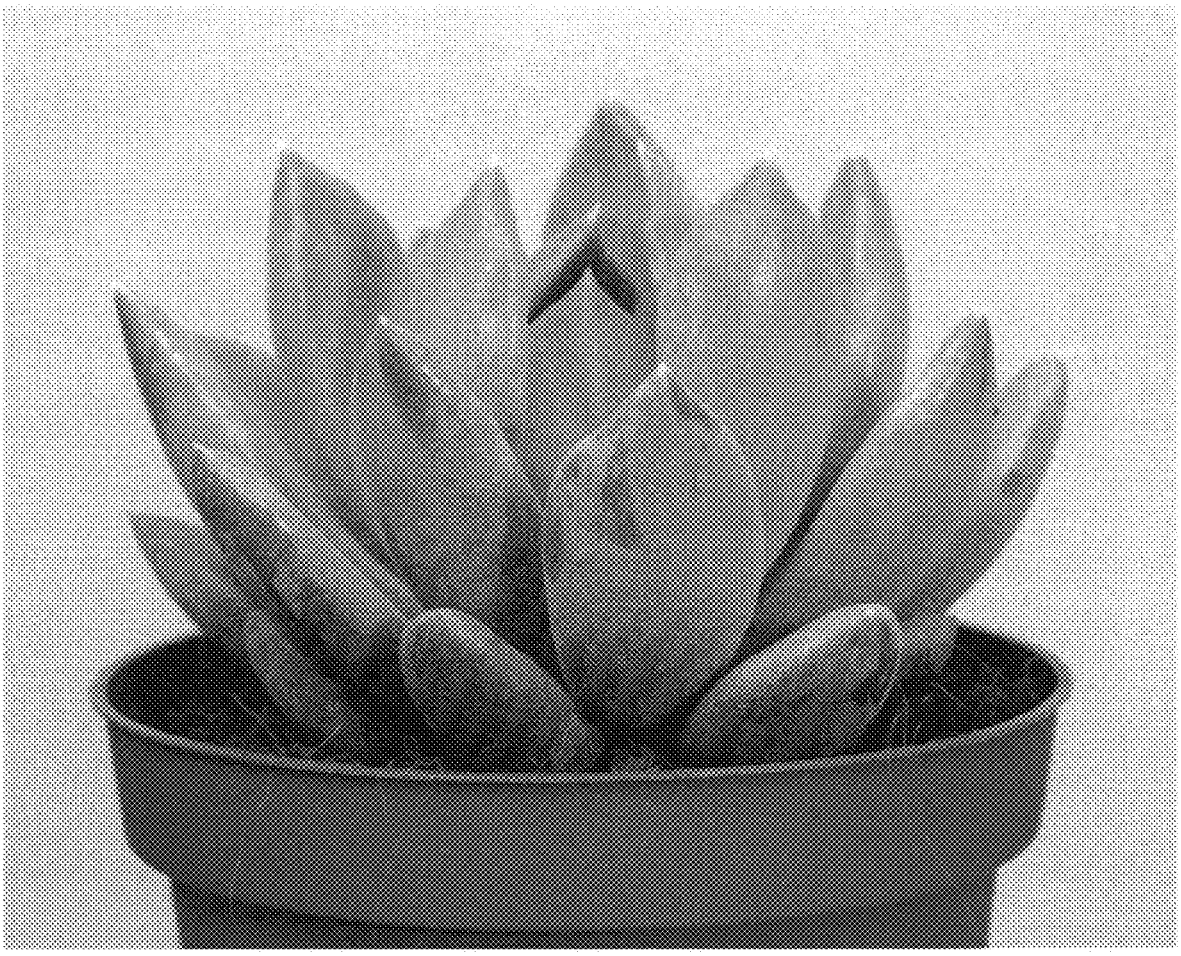
FIG. 1 illustrates, as nearly true as it is reasonably possible to make the same in color photographs of this type, an exemplary plant of 'AMIECH1702' grown in a commercial greenhouse in Heerhugowaard, the Netherlands. This plant is approximately 10 months old, shown planted in a 12 cm container.
Figure 2:
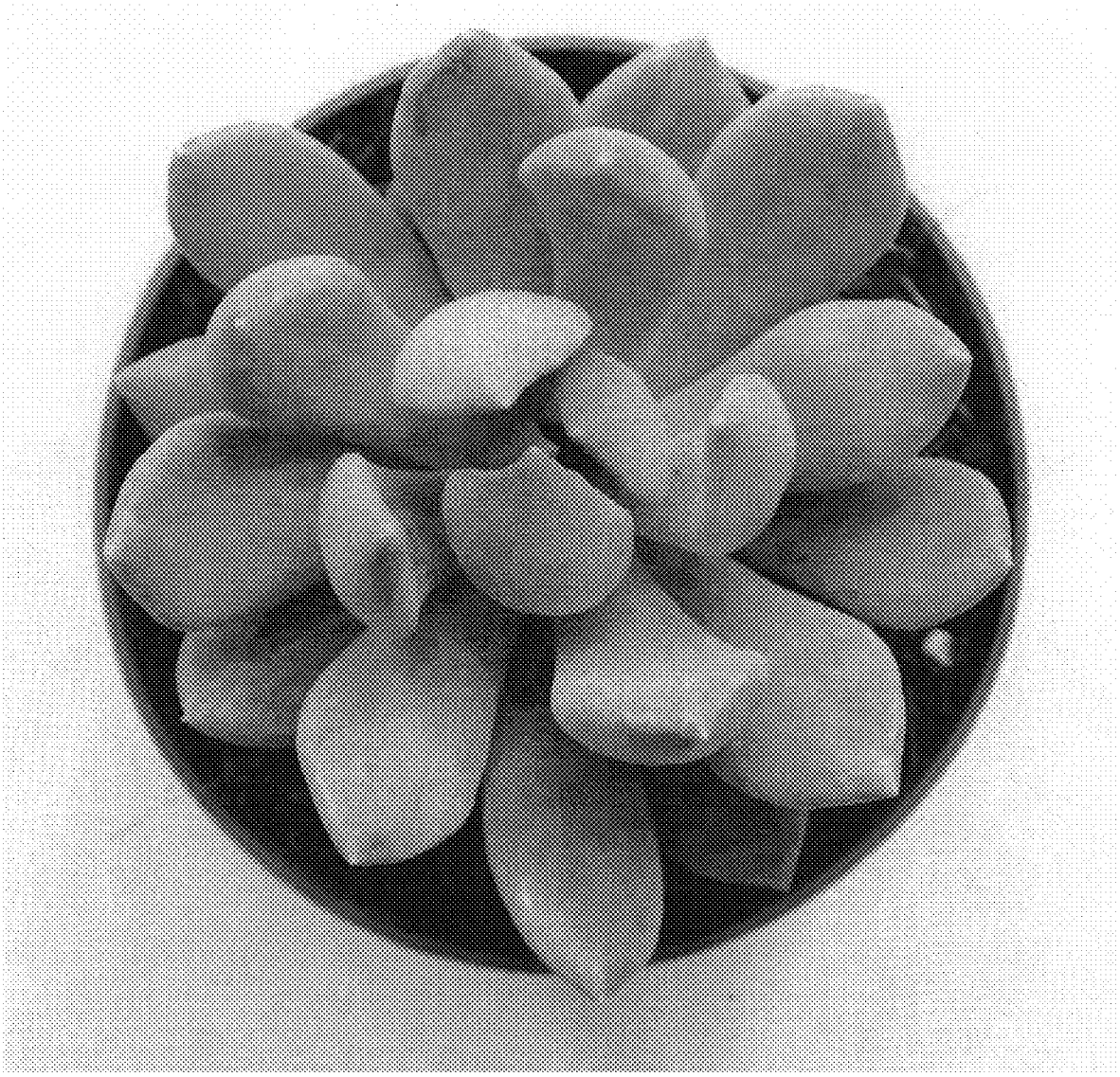
FIG. 2 illustrates, as nearly true as it is reasonably possible to make the same in color photographs of this type, the typical foliage arrangement of 'AMIECH1702'.
Figure 3:
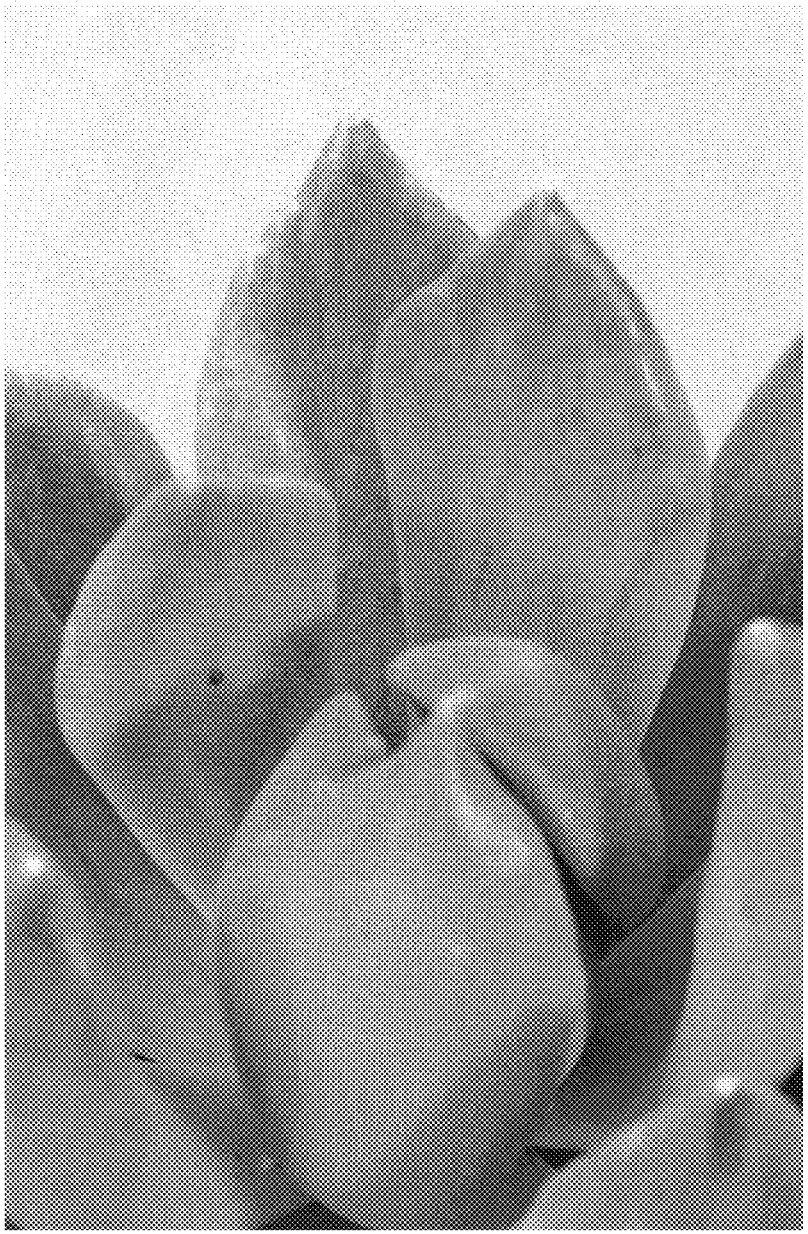
FIG. 3 illustrates, as nearly true as it is reasonably possible to make the same in color photographs of this type, the adaxial surface of the mature foliage 'AMIECH1702'.
Figure 4:
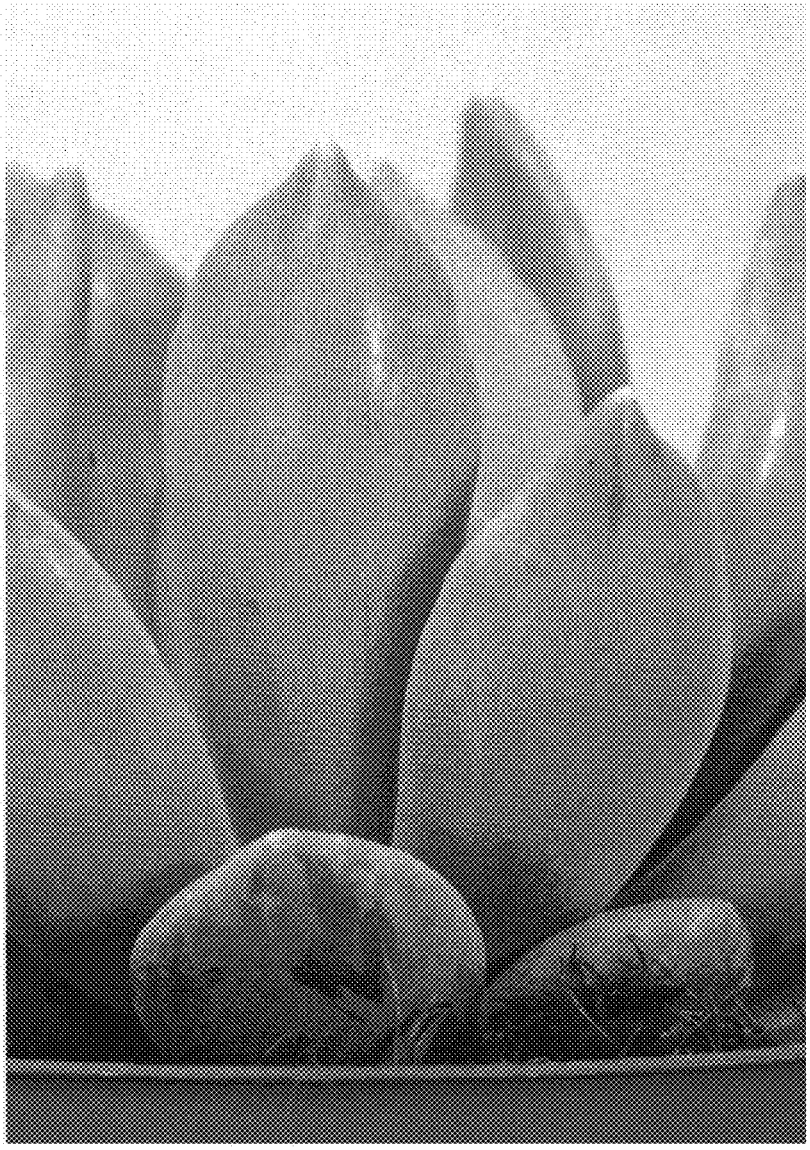
FIG. 4 illustrates, as nearly true as it is reasonably possible to make the same in color photographs of this type, the abaxial surface of the mature foliage 'AMIECH1702'.

The following observations and measurements made in January of 2018 describe averages from a sample set of six specimens of 10 months old 'AMIECH1702' plants grown in 12 cm nursery containers at commercial greenhouse in Heerhugowaard, the Netherlands. Plants were produced using conventional greenhouse production protocols for *Pachyveria* plants which consisted of minimal irrigation and fertilizer applications, and chemical pest and disease control measures against mealy bug and *Botrytis* as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'AMIECH1702' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'AMIECH1702' and comparisons with the parent plants and closest known comparator are provided below.

Plant description:

*Growth habit.*—Succulent perennial with foliage growing in a non-branched basal rosette.

*Plant shape.*—Flattened globular.

*Height from soil level to top of foliar plane.*—7.1 cm.

*Plant spread.*—Average of 10.0 cm.

*Growth rate.*—Low to moderate.

*Plant vigor.*—Low to moderate.

*Propagation.*—Type — Leaf cuttings. Time to initiate rooting — Approximately 21 to 35 days at 18 degrees Celsius. Crop time — Approximately 18 to 22 weeks to produce a marketable plant in a 7 cm container.

*Disease and pest resistance or susceptibility.*—Neither resistance nor susceptibility to typical *Pachyveria* pests and diseases has been observed.

*Environmental tolerances.*—Adapt to, at least, USDA Zones 10 to 12 and temperatures as high as 40 degrees Celsius; moderate tolerance to rain yet drought tolerant once established; high tolerance to wind.

Root system:

*General.*—Fine, well-branched fibrous roots.

Stems:

*Branching habit.*—Leaves in a non-branching basal rosettes; no main branches or lateral branches present.

Foliage:

*Arrangement.*—Rosette.

*Division.*—Simple.

*Attachment.*—Sessile.

*Quantity.*—Approximately 25 leaves per rosette.

*Shape.*—Thick, succulent leaves which are spatulate to obovate.

*Dimensions.*—5.9 cm long, 3.2 cm wide, and 1.0 cm thick, on average.

*Aspect.*—Very slightly concave and slightly curved upward.

*Attitude.*—Upright.

*Apex.*—Acute to apiculate.

*Base.*—Cuneate.

*Margin.*—Entire except near the apex which is very slightly crenate to sinuate; not undulated or lobed.

*Pubescence, texture and luster of the adaxial surface.*—Glabrous, smooth, and matte; lightly to moderately glaucous.

*Pubescence, texture and luster of the abaxial surface.*—Glabrous, smooth, and matte; lightly to moderately glaucous.

*Color.*—Juvenile foliage, adaxial surface — Yellow-green, nearest to RHS 148D, and fading to in between yellow-green and greyed-green towards the base, nearest to in between RHS 145C and 193C; the epicuticular glaucous wax covering the leaf surface is greyed-green, nearest to RHS 188D. Juvenile foliage, abaxial surface — Yellow-green, nearest to RHS 148D, and fading to in between yellow-green and greyed-green towards the base, nearest to in between RHS 145D and 193D; the epicuticular glaucous wax covering the leaf surface is greyed-green, nearest to RHS 188D. Mature foliage, adaxial surface — Yellow-green, nearest to RHS 148B, and fading to greyed-green towards the base, nearest to RHS 195B; the epicuticular glaucous wax covering the leaf surface is greyed-green, nearest to RHS 188D. Mature foliage, abaxial surface — Yellow-green, nearest to RHS 148B, and fading to greyed-green towards the base, nearest to RHS 194B; the epicuticular glaucous wax covering the leaf surface is greyed-green, nearest to RHS 188D. Venation — No venation is visible.

*Petiole.*—No petiole; leaves are sessile.

Inflorescence: No flowering has been observed to date.

COMPARISONS WITH THE PARENT PLANT AND CLOSEST KNOWN COMPARATOR

Plants of the new cultivar 'AMIECH1702' differ from the seed parent, an unnamed *Echeveria lilacina* plant (not patented), in the following characteristics described in Table 1 below.

TABLE 1

| Characteristic | 'AMIECH1702' | *Echeveria lilacina* seed parent. |
|---|---|---|
| Plant size. | Larger than the seed parent. | Smaller than 'AMIECH1702'. |
| Foliage thickness. | Thicker and more rounded than the seed parent. | Thinner and flatter than 'AMIECH1702'. |
| General coloration of the foliage. | Greyed-green with a blue hue. | White with a lilac hue. |

Plants of the new cultivar 'AMIECH1702' differ from the pollen parent, an unnamed *Pachyphytum oviferum* plant (not patented), in the following characteristics described in Table 2 below.

TABLE 2

| Characteristic | 'AMIECH1702' | *Pachyphytum oviferum* pollen parent. |
|---|---|---|
| Branching habit. | Leaves in a non-branching basal rosettes; no stem present. | Leaves in a basal rosettes, eventually forming a short, unbranched stem with age. |
| Foliage cross-section. | Thinner and flatter than the parent. | Thicker and more rounded than 'AMIECH1702'. |
| Foliage apex. | Acute to acuminate. | Obtuse. |

Plants of the new cultivar 'AMIECH1702' differ from the closest known commercial comparator, *Echeveria* x *Pachypythum* hybrid 'TSAECH1805' (U.S. Plant patent application Ser. No. 16/501,048), in the following characteristics described in Table 3 below.

TABLE 3

| Characteristic | 'AMIECH1702' | 'TSAECH1805' |
|---|---|---|
| Plant size. | Smaller than 'TSAECH1805'. | Larger than 'AMIECH1702'. |
| Foliage abundance. | Less abundant than 'TSAECH1805'. | More abundant than 'AMIECH1702'. |
| Foliage shape. | Spatulate to obovate. | Narrowly obovate to obovate. |
| General coloration of the foliage. | Greyed-green with a blue hue. | Generally appearing to be blue-gray and becoming progressively darker towards the outer whorls of foliage; lightly suffused and margined greyed-orange towards the apex. |

That which is claimed is:

1. A new and distinct variety of *Echeveria lilacina* x *Pachyphytum oviferum* hybrid plant named 'AMIECH1702', substantially as described and illustrated herein.

* * * * *